United States Patent
Pike et al.

(10) Patent No.: US 8,623,605 B2
(45) Date of Patent: Jan. 7, 2014

(54) DIAGNOSTIC ASSAY FOR SPONGIFORM ENCEPHALOPATHIES

(75) Inventors: Ian Hugo Pike, Tonbridge (GB);
Malcolm Andrew Ward, Shefford (GB);
Darragh Patrick William O'Brien, London (GB)

(73) Assignee: Electrophoretics Limited, Coham Surrey (GB)

( * ) Notice: Subject to any disclaimer, the term of this patent is extended or adjusted under 35 U.S.C. 154(b) by 0 days.

(21) Appl. No.: 12/302,994

(22) PCT Filed: May 29, 2007

(86) PCT No.: PCT/GB2007/050302
§ 371 (c)(1),
(2), (4) Date: Dec. 1, 2008

(87) PCT Pub. No.: WO2007/138357
PCT Pub. Date: Dec. 6, 2007

(65) Prior Publication Data
US 2009/0197270 A1   Aug. 6, 2009

(51) Int. Cl.
*G01N 33/53* (2006.01)
*G01N 33/567* (2006.01)
*G01N 33/566* (2006.01)
*C12Q 1/37* (2006.01)

(52) U.S. Cl.
USPC ............. 435/7.1; 435/7.21; 435/7.8; 435/7.9; 435/7.92; 435/23; 436/501; 436/503

(58) Field of Classification Search
None
See application file for complete search history.

(56) References Cited

PUBLICATIONS

Gray et al., 2006, Biochem. Soc. Transcripts, vol. 34, pp. 51-54.*
Tagliavini et al., 2001, J. Biol. Chem., vol. 276, No. 8, pp. 6009-6015.*
Allegretto, E. et al., "Immunochemical Detection of Unique Proteolytic Fragments of the Chick 1,25-Dihydroxyvitamin D3 Receptor", The Journal of Biological Chemistry, vol. 262, No. 3, Jan. 25, 1987, pp. 1312-1319.
Cohen, S. et al., "Probing the solution structure of the DNA-binding protein Max by a combination of proteolysis and mass spectrometry", Protein Science, Cambridge University Press, Mar. 24, 1995, pp. 1088-1099.
Dent, J. et al., "Identification of a cleavage site directing the immunochemical detection of molecular abnormalities in type IIA von Willebrand factor", Proc. Natl. Acad. Sci, vol. 87, Aug. 1990, pp. 6306-6310.
J. Collinge, "Prion Diseases of Humans and Animals: Their Causes and Molecular Basis", Annual Review of Neuroscience, vol. 24, Mar. 2001, pp. 519-550.
Y. Zhang, et al., "Up-regulation of cathepsin B and cathepsin L activities in scrapie-infected mouse Neruo2a cells", Journal of General Virology, vol. 84, May 6, 2003, pp. 2279-2283.

* cited by examiner

*Primary Examiner* — Olga N Chernyshev
(74) *Attorney, Agent, or Firm* — Arent Fox LLP

(57) ABSTRACT

The invention provides a method of diagnosis of a spongiform encephalopathy in a diagnostic sample of a valid body tissue taken from a subject, which comprises detecting an increased proteolytic activity in the diagnostic sample, compared with a sample from a control subject.

18 Claims, 5 Drawing Sheets

Figure 2 Negative FRET assay format

Figure 4 Secondary Albumin Fragments (SAF's) as Biomarkers of vCJD and other neurological disorders

DIAGNOSTIC ASSAY FOR SPONGIFORM ENCEPHALOPATHIES

CROSS-REFERENCE TO RELATED APPLICATION

This application is a National Stage entry of International Application No. PCT/GB2007/050302, filed May 29, 2007. The disclosure of the prior application is hereby incorporated herein in its entirety by reference.

SEQUENCE LISTING

The instant application contains a Sequence Listing which has been submitted via EFS-Web and is hereby incorporated by reference in its entirety. Said ASCII copy, created on Mar. 30, 2010, is named 10814093.txt and is 2,505 bytes in size.

BACKGROUND OF THE INVENTION

1. Field of the Invention

This invention relates to methods of diagnosing whether an individual has a spongiform encephalopathy, the stage of disease and the efficacy of treatment for the disease.

2. Description of the Related Art

Spongiform encephalopathies are neurodegenerative diseases of the central nervous system. They can be transmitted, inherited or occur sporadically and are observed in animals, e.g. as bovine spongiform encephalopathy (BSE) in cattle or scrapie in sheep, as well as in humans as Creutzfeldt-Jakob disease (CJD), Gerstman Sträussler Scheinker syndrome, Fatal Familial Insomnia or Kuru. They have a long incubation period, leading to ataxia, dementia, psychiatric disturbances and death. Neuropathological changes include vacuolar degeneration of brain tissue, astrogliosis and amyloid plaque formation. The diseases are difficult to diagnose pre-mortem.

SUMMARY OF THE INVENTION

The invention provides the following:

1. A method of diagnosis of a spongiform encephalopathy in a diagnostic sample of a valid body tissue taken from a subject, which comprises detecting an increased proteolytic activity in the diagnostic sample, compared with a sample from a control subject.
2. A method according to 1, in which the increased proteolytic activity is detected by means of a greater abundance in the diagnostic sample, compared with the control sample, of smaller fragments of a target protein which is a substrate of the proteolytic activity.
3. A method according to 2, in which the target protein is a protein which occurs naturally in the subject.
4. A method according to 2, in which the target protein is a synthetic polypeptide.
5. A method according to any of 2 to 4, in which the proteolytic activity involves specific cleavage at a -VK- motif in the target protein.
6. A method according to any of 2, 3 and 5, in which the target protein is residues 2-78 or 2-80 of albumin, and the smaller fragments are residues 41-78 or 41-80 of albumin.
7. A method according to any of 2, 3 and 5, in which the target protein is residues 18-38 of ACTH, and the smaller fragment is residues 18-20 of ACTH.
8. A method according to any of 2, 4 and 5, in which the target protein is SEQ ID NO: 2 and the smaller fragments are residues 1-22, 22-42, 43-63 and 64-84 of SEQ ID NO: 2.
9. A method according to any of 2 to 8, in which the target protein is an immobilised reporter peptide having a detectable label.
10. A method according to 9, in which the immobilised reporter peptide is cleaved by the proteolytic activity resulting in at least one immobilised fragment and at least one liberated fragment, and the detectable label is differentially present between the immobilised fragment and the liberated fragment.
11. A method according to 10, in which the detectable label is associated with the liberated fragment.
12. A method according to 9, in which the detectable label is present as a cooperating pair of reporter groups straddling a cleavage point in the reporter peptide, whereby after cleavage the pair is separated between an immobilised fragment and a liberated fragment.
13. A method according to 12, in which the pair of reporter groups cooperate to produce no signal when together in the uncleaved peptide, but generate a signal when separated after cleavage of the peptide.
14. A method according to 12, in which the pair of reporter groups cooperate to generate a signal when together in the uncleaved peptide, but cease to generate a signal when separated after cleavage of the peptide.
15. A method according to any of 1 to 14, in which the valid body tissue is a body fluid.
16. A method according to 15, in which the body fluid is blood, plasma or serum.
17. A method according to any of 1 to 14, in which the valid body tissue is of brain, nerve, tonsillar, spleen or other lymphoreticular tissue.
18. A method according to any of 1 to 17, in which a particular stage of the spongiform encephalopathy is diagnosed.
19. A method according to 18, in which the progression of the spongiform encephalopathy in a subject is monitored by carrying out diagnoses on samples taken at intervals from the same subject.
20. A method according to any of 1 to 19, in which the spongiform encephalopathy is selected from Creutzfeldt-Jakob disease (CJD), variant CJD, Gausman-Straussler syndrome (GSS), fatal insomnia, bovine spongiform encephalopathy (BSE), scrapie, chronic wasting disease (CWD) and experimental infections of any of the above established in experimental animals or cell lines

DEFINITIONS

The term "diagnosis" includes determining whether spongiform encephalopathy is present or absent and also includes determining the stage to which it has progressed (or regressed in the course of treatment). The diagnosis can serve as the basis of a prognosis as to the future outcome for the subject. The diagnosis can be made either pre-mortem or post mortem.

The term "spongiform encephalopathy" includes Creutzfeldt-Jakob disease (CJD), variant CJD, Gausman-Straussler syndrome (GSS), fatal insomnia, bovine spongiform encephalopathy (BSE), scrapie, chronic wasting disease (CWD) and experimental infections of any of the above established in experimental animals or cell lines.

The terms "individual", "subject" and "patient" mean a mammal susceptible to spongiform encephalopathy, and most commonly will be human, cow, sheep, mouse, rat or deer.

The term "valid body tissue" means any tissue in which it may reasonably be expected that an increased proteolytic activity related to spongiform encephalopathy may be found.

It will most commonly be a body fluid, e.g. blood or a blood derivative such as plasma or serum. It may also be brain, nerve, tonsillar, spleen or other lymphoreticular tissue.

The term "increased" in relation to proteolytic activity means increased sufficiently significantly to be detectable by the experimental methodology used, and usually increased by a factor of at least 2 relative to the control. It does not imply that a step of comparing is actually undertaken, since in many cases it will be obvious to the skilled practitioner that the activity is abnormally high or low. Further, when the stages of spongiform encephalopathy are being monitored progressively, or when a course of treatment is being monitored, the comparison made can be with the activity previously seen in the same subject at an earlier stage of progression of the disease, or at an earlier stage of treatment or before treatment has commenced.

The term "control" refers to a normal subject, i.e. one not suffering from spongiform encephalopathy, or to healthy tissue of the same subject as the diagnostic sample.

The term "protein" encompasses a polypeptide and may be either naturally occurring or synthetic or a hybrid.

BRIEF DESCRIPTION OF THE FIGURES

FIG. 4 discloses the "Mature Human Albumin Residues 1-100" as SEQ ID NO: 3.

DETAILED DESCRIPTION

Figure 1:
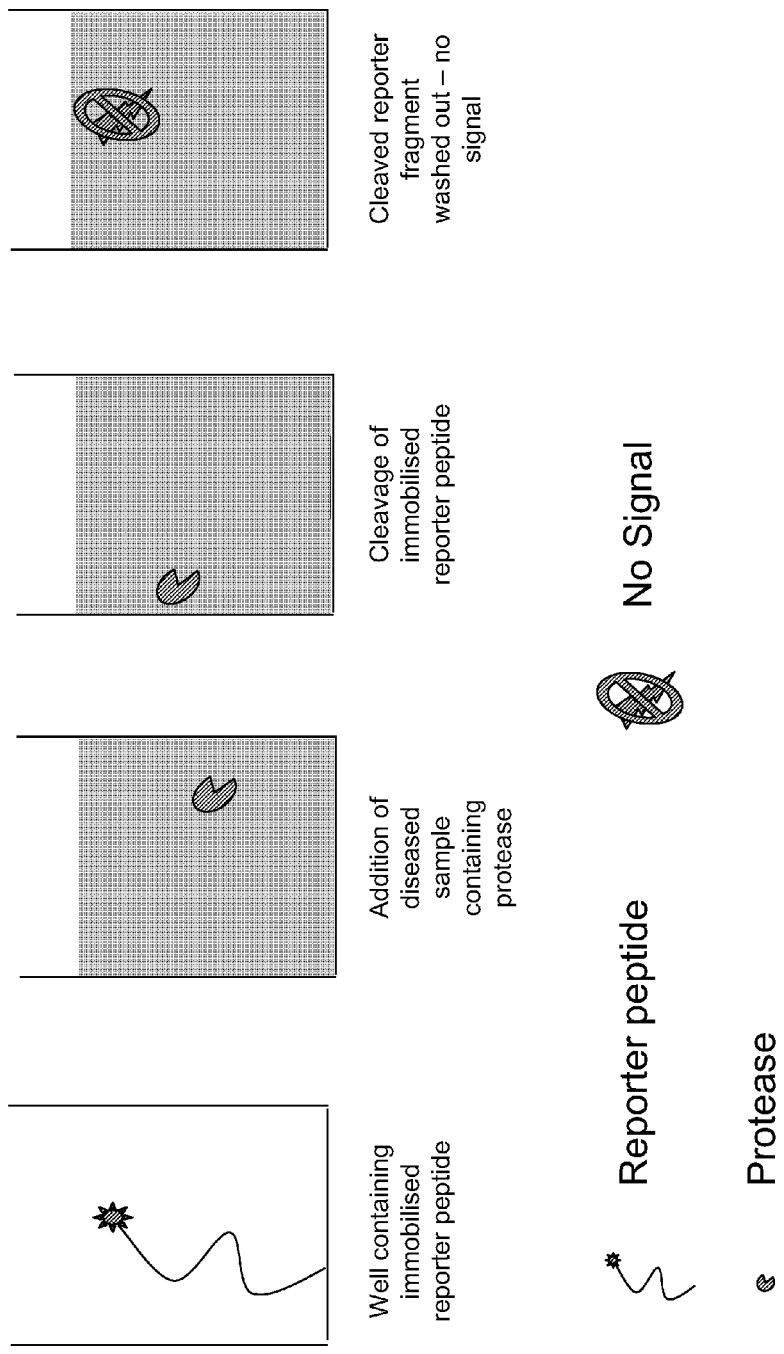
FIG. 1 is a diagrammatic representation of a standard assay format according to an embodiment of the invention.

The invention relies on our finding that in the blood of patients with spongiform encephalopathies there are readily detectable protein fragments associated with the disease state and which are different to the non-diseased state. In particular we have noted that in diseased individuals we see an increase in the lower molecular weight daughter fragments of a protein with a concomitant loss of the higher molecular weight parent fragment which is therefore more abundant in non-diseased individuals. We have termed the mechanism by which this process is achieved as Secondary Activated Fragmentation (SAF) since in most cases the parent is itself a fragment of a full length protein which is then further processed in a disease specific manner. We hypothesise that in the case of spongiform encephalopathies this is due to the expression of disease specific proteases though we have yet to identify the enzymes responsible. It is not necessary for this invention to identify the protease responsible for the SAF.

We present in this invention a method of detecting vCJD through the monitoring of SAF on a fragment of serum albumin (SwissProt Accession No. P02768) which has a molecular weight of approximately 8,644 Da and which in disease is processed to yield two smaller fragments of 4,340 and 4,132 Da respectively (further details of this work are described in Example 1 below). Whilst these patterns can be followed using the discovery methodology, namely Surface Enhanced Laser Desorption Ionisation-Time of Flight (SELDI-TOF) mass spectrometry, it would be preferable to provide a simpler, more rapid and much less expensive means of monitoring the SAF of albumin and indeed several other proteins.

We have therefore developed a simple biological monitoring assay that can be performed using a wide variety of solid surface substrates, recombinant proteins and reporter systems to yield a diagnostic result. The assay formats can be developed for standard colourimetric, fluorescent or chemoluminescent read out, or can include fluorescent resonance energy transfer (FRET) techniques to allow real time measurement of SAF.

The assay is based on the provision of a synthetic peptide corresponding to the protein region of interest that contains the SAF cleavage site. Such sites can be readily determined by identifying the parent and daughter fragments through mass spectrometry and subsequently identifying the site of cleavage. A synthetic peptide of between 10 and 100 amino acids is most preferable, though peptides up to the full length of the parent fragment can be used.

In one embodiment of this invention the synthetic peptide contains a group at one terminus that allows immobilisation onto a solid surface, and at the other terminus it carries a reporter molecule. In this context the reporter molecule may be a specific epitope that can be detected by a specific antibody (whose binding can subsequently be measured) or it may be directly labelled with an enzyme capable of producing a clourimetric or chemoluminescent signal, or a fluorophore.

In a second embodiment of the invention two FRET molecules can be incorporated into the synthetic peptide around the cleavage site such that by the mechanism of the FRET there is no detectable fluorescence when the synthetic peptide remains uncleaved. The method of incorporation must be such that cleavage of the synthetic peptide by the disease related protease is maintained. Upon cleavage the close spatial relationship of the FRET pair is lost and both molecules can be freely detected in a standard fluorimeter equipped with the necessary excitation and detection filters. The invention is not particularly limited by the nature of the fluorophores in the FRET pair or their excitation and emission wavelengths. For example the FRET pair may be tuned so as to emit a signal whilst they remain physically close in the intact synthetic peptide with the signal being lost on cleavage.

In an embodiment of the invention a solid substrate bearing such a labelled synthetic peptide according to any of the previously described aspects of the invention is incubated with serum from an individual suspected of suffering from a spongiform encephalopathy. Proteases specifically present in the blood from a diseased individual will cleave the synthetic peptide by the mechanism of SAF whereas a healthy individual will lack the protease and so no processing would occur. By means of loss of the reporter molecule distal to the anchored terminus, or a change in the FRET fluorescence pattern at the cleavage site of the synthetic peptide, the rate and/or extent of the cleavage process can be measured.

Figure 2:
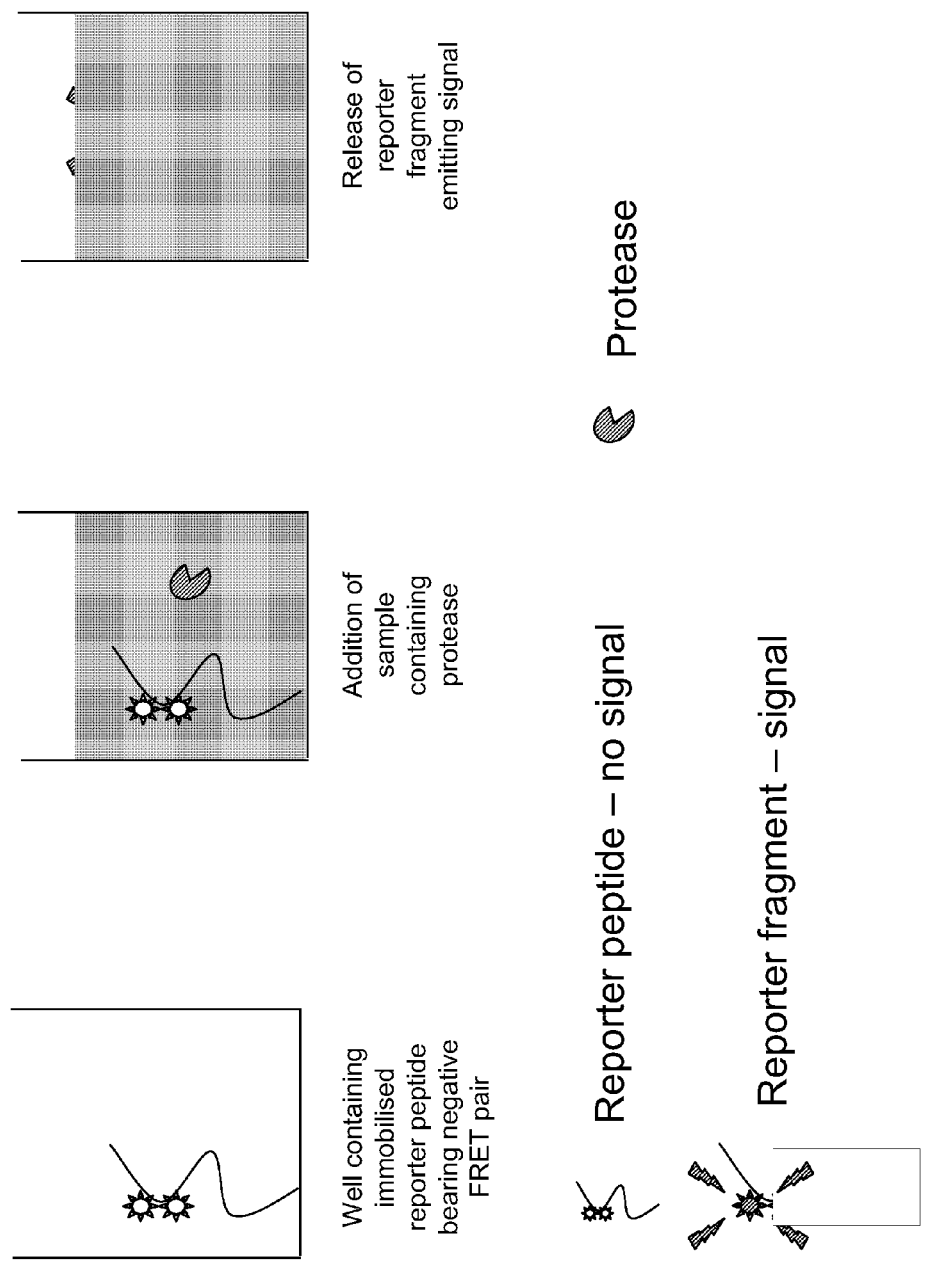
FIG. 2 is a diagrammatic representation of a negative FRET assay format.
Figure 3:
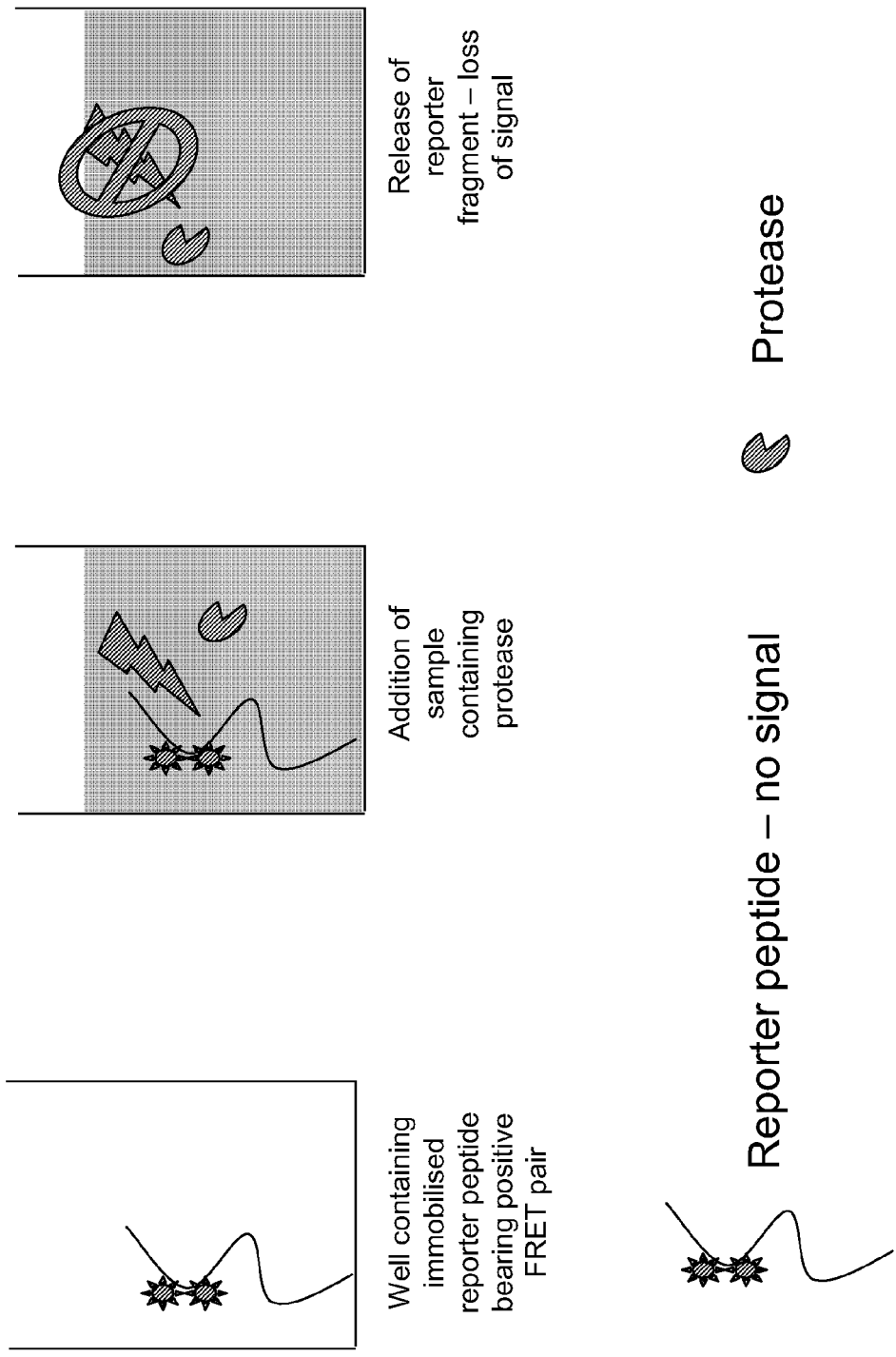
FIG. 3 is a diagrammatic representation of a positive FRET assay format.

The three basic, negative FRET and positive FRET assay formats are shown in FIGS. 1 to 3. It will be obvious to the skilled artisan that there are a number of additional means of detecting whether the cleavage event has occurred or not. Such other methods are included within the scope of the invention.

In a further aspect of the invention the processing of the parent synthetic peptide can be monitored using mass spectrometry.

The following Examples illustrate the invention.

Example 1

Secondary Albumin Fragments as Biomarkers of vCJD and Other Neurological Disorders A set of vCJD biomarkers was revealed using Surface Enhanced Laser Desorption Ionisation (SELDI) time of flight mass spectrometry. Experiments to establish the identity of these new candidates are also described. Although other biomarkers were found, the following description is restricted to secondary albumin fragments.

1.1 Sample Preparation for SELDI Discovery

Plasma samples from clinically confirmed cases of vCJD (n=10), neurological controls (HD) (n=10) and non-diseased control (n=10) patients were collected from the MRC Prion unit. Two microliters of each of the depleted samples were diluted in 3 μl of lysis buffer containing 9.5 M urea, 2% CHAPS, 0.8% pharmalyte pH 3-10, 1% DTT and protease inhibitor and undepleted samples were diluted in the same ratio using the above lysis buffer without pharmalyte.

1.2 Plasma Depletion

Albumin and IgG were removed from the plasma using a commercially available resin (GE Healthcare). This kit is antibody based and contains a resin that specifically removes albumin and IgG directly from whole human serum and plasma samples. It is claimed that >95% albumin and >90% IgG from 15 μl human serum/plasma can be achieved, thereby increasing the resolution of lower abundance proteins. A microspin column is used through which the unbound protein is eluted.

Depletion was carried out according to the manufacturer's instructions using a starting volume of 15 μl of crude plasma sample. The resulting depleted sample was acetone precipitated (as recommended in the instructions of the kit) and re-suspended in standard 2DE lysis buffer.

1.3 Surface Enhanced Laser Desorption Ionisation (SELDI) Mass Spectrometry

Profiling of depleted plasma samples was performed using an eight spot strong anion exchange (Q10) protein chip array and profiling of undepleted plasma was performed using both the eight spot Q10 and weak cation exchange (CM10) protein chip arrays. All samples were run in duplicate and in a randomised manner. Essentially, all the Q10 and CM10 chips were equilibrated four times in the appropriate wash buffer. For Q10 chips, 100 mM Tris HCl pH 9.0 was used as the wash buffer and for CM10 the wash buffer was 50 mM sodium acetate pH 7.5. 5 μl of the diluted samples were applied to each spot and this was then incubated in a humidity chamber for 45 minutes. Samples were carefully removed and the chips were washed four times in the appropriate wash buffer and one wash with 18.2 MΩ water. 0.6 μl matrix solution containing 20 mg/ml sinnapinic acid (Ciphergen) in 50% acetonitrile (Fisher Scientific) and 0.5% trifluoroacetic acid was applied twice to each spots. Data acquisition was performed using a PBS-II reader (Ciphergen Biosystems). Spectra were acquired using a summation of 155 shots with a laser intensity of 200, detector sensitivity of 8 and a focus mass m/z 25000. Baseline subtraction and normalisation on total ion count were performed on all the spectra. Internal calibration of each spectra was undertaken using a minimum of 2 peaks in each spectrum.

1.4 SELDI Data Analysis

Pre-Processing:

All data were imported to the SIMCA-P software package (Umetrics). Variables corresponding to masses below m/z 2,500 were excluded due to the considerable chemical noise in this region. The remaining variables corresponding to masses between m/z 2,500 and m/z 100,000 were centered to the mean value and Pareto scaled.

Principal Component Analysis (PCA):

PCA models were fitted to the data sets with as many components (A) as would fit following the internal rules SIMCA-P uses to determine the significance of the components (Eriksson et al. 2001). The goodness of fit ($R^2$) and goodness of prediction ($Q^2$) parameters were used to assess the usefulness of each of the subsequent components fitted in the model. The automatically fitted components were inspected and kept as long as the $Q^2$ parameter was increasing. The cumulative $R^2$ parameter for the final accepted component gave the total proportion of variance in the data explained by the model. Plots were produced displaying the observation scores (t) and variable loadings (p) for pairs of principal components (a). The scores plots were inspected to look for patterns of systematic variation and outlying observations that could hamper later classification efforts. In particular, the positions of observations analysed on each chip were scrutinised to check for unusual chips. The reproducibility of duplicated sample analyses were also checked using the scores plots. The Ellipse shown on the scores plots corresponds to Hotelling's $T^2$ at 95%, a multivariate adaptation of a confidence region. For a data set with a multivariate normal distribution, 95% of the observations would be expected to lie within the region encompassed by the Ellipse, thus observations that are a long way outside the ellipse may represent problems to be investigated and addressed. Trends found through inspection of the scores plots were interpreted through inspection of the variables found on the corresponding loadings plots. Individual m/z values plotted at the extremes of the plot were considered to be most influential on the separation of the groups. Interestingly, such plots tend to show several consecutive m/z datapoints, which effectively describe the original peak observed in the SELDI profiles themselves.

Partial Least Squares Data Analysis (PLS-DA) and Modelling:

Components (A) of PLS-DA models were fitted to the data sets as long as they met the criteria used by SIMCA-P to determine the significance of components (Eriksson et al. 2001). As for the PCA modelling, the $R^2$ and $Q^2$ parameters were inspected to determine which components should be included in the model. Unlike the PCA modeling, PLS-DA models posses $R^2$ values describing the fit of the model to both the X (measurement) variables and the Y (class) variables. Plots were produced displaying the observation scores (t) and the variable weights (w*c) for pairs of PLS components (a). Because each PLS component is fitted so as to both approximate the X and Y data well and maximize the correlation between the X and Y data, in practice the first one or two components usually separate the observations well when there are few groups present in the data set. The interpretation of the PLS scores and weights plots is similar to that used to interpret a PCA model, with the PLS weights being analogous to the PCA loadings. Hotelling's $T^2$ was computed and displayed on all PLS scores plots to help identify deviating observations.

The two parameters referred to as variable influence on projection (VIP) and PLS coefficients (COEFF) were used to determine which of all the masses measured in the SELDI spectral data were most important in defining the model parameters and explaining the groups. Specific thresholds were determined empirically and used to exclude those variables with VIP and COEFF values lower than the threshold. The ability of the PLS-DA models generated to correctly predict the class of (new) samples was determined by 2-fold cross-validation. Cross-validation was performed by dividing the data set into a training and a test set. A PLS-DA model was fitted to the training portion of the data set and subsequently used to predict the classes of the test portion of the data set. The training and test data sets were then swapped and the process repeated. The number of correct and incorrect classifications from both rounds of testing were recorded and used to calculate sensitivities and specificities of the predictions. This cross-validation method was used to test both the models built using the data set containing all variables and those built following variable selection (as described above).

Univariate Methods:

Statistical significance testing was performed using the Protein Chip software (Ciphergen Biosystems). Mann-Whitney (Wilcoxon) tests for two independent samples were used. Peak detection and matching were performed using the Protein Chip software and this data was then submitted to the Biomarker Wizard module for analysis. The p-value was taken as the result of the test. The data for each of the marked peaks was also exported to Excel (Microsoft) as peak intensities to calculate the fold change criteria for each peak. Because of the skewed distributions observed for the areas or intensities of each set of matched peaks, the data were $\log_{10}$ transformed prior to calculation of the mean and median values of the distributions as well as the standard deviations. The parameters of the distributions were then transformed back onto the original scales in order to calculate fold-changes and effect sizes. Fold-changes were calculated by dividing the larger of the mean (or median) values by the smaller value of two groups, yielding a value greater than or equal to one. Effect size (Cohen's D) was calculated as the difference between the mean values of two groups divided by the pooled standard deviation.

1.5 Candidate Identification

Having produced/created a list of candidate peaks of interest corresponding to each chip surface, the identity of the proteins responsible for each discriminating peak was determined.

Material was extracted directly from the chip surface and following electrophoretic separation and enzymatic digestion proteins were identified by electrospray tandem mass spectrometry (LC/MS/MS).

Bands of interest were excised from the silver stained gel and "in-gel" reduction, alkylation and digestion with trypsin were performed prior to subsequent analysis by LC/MS/MS. Peptides were extracted from the gel pieces by a series of acetonitrile and ammonium bicarbonate washes. The extract was pooled with the initial supernatant and lyophilised. Each sample was then resuspended in 23 μl of 50 mM ammonium bicarbonate. Chromatographic separations were performed using an Ultimate LC system (Dionex, UK). Peptides were resolved by reversed phase chromatography on a 75 μm C18 PepMap column. A gradient of acetonitrile in 0.05% formic acid was delivered to elute the peptides at a flow rate of 200 nl/min. Peptides were ionised by electrospray ionisation using a Z-spray source fitted to a QTof-micro (Waters Corp.). The instrument was set to run in automated switching mode, selecting precursor ions based on their m/z and intensity, for sequencing by collision-induced fragmentation.

The mass spectral data was processed into peak lists (containing the precursor ion m/z and charge state and the m/z and intensity of the fragment ions. Database searching was undertaken to establish the identity of the protein(s) present. This was performed using the Mascot search algorithm against the NCBI non-redundant (nr) and SWISS-PROT databases.

Once proteins were identified the expected molecular weight of the mature proteins was extrapolated from the information contained within the database entry and correlated with the molecular weight determined experimentally in the original SELDI profiles. In this way it was possible in most cases to assign related species to a single protein sequence.

2.1 SELDI Data Analysis

Following extensive analysis using multivariate techniques and Mann-Whitney tests, the depleted plasma study (Q10 SAX chip) revealed variation in several peaks, which discriminate between vCJD and control samples. Four peaks relating to albumin fragments are shown in Table 1 below.

TABLE 1

SELDI peaks of interest discriminating between vCJD and control samples (depleted plasma study using Q10 SAX chip)

| Candidate Reference number | Peak of Interest | p-value[a] | Fold-Change (mean)[b] | Fold-change (median)[c] | Direction of change | Cohen's D[d] |
|---|---|---|---|---|---|---|
| P1 | 8644 | 0.023 | 2.47 | 3.19 | Decreased | 1.130 |
| P2 | 8856 | 0.045 | 1.75 | 1.95 | In CJD | 0.934 |
| P3 | 4132 | 0.001 | 3.87 | 5.16 | Increased | 1.743 |
| P4 | 4340 | 0.011 | 1.85 | 1.93 | in CJD | 1.136 |

Notes:
[a] p-values computed for a Mann-Whitney test (not corrected for multiple testing).
[b] Mean and median peak intensity values for each group were estimated after $\log_{10}$ transformation of the data. The estimates were transformed back to the original scale prior to calculating fold-changes.
[c] The effect size (Cohen's D) is computed as the different between the means divided by the pooled standard deviation.

2.2 Candidate Identification

The results suggest that a collection of human albumin fragments exist in the SELDI profiles and that these differ in abundance when vCJD cases are compared to controls. It is apparent that these relate to the N terminal region of the protein in particular. The peaks P1 to P4 are related to N-terminal fragments of Human albumin and further details are given in Table 2 below.

TABLE 2

List of Candidate biomarkers matched to fragments within the N-terminal region of Human Albumin

| Candidate Ref# | [M + H]+ observed m/z | Expected Average Mr | Residues | % Error |
|---|---|---|---|---|
| P1 | 8644 | 8642 | 2-78 | 0.020 |
| P2 | 8856 | 8857 | 2-80 | 0.010 |
| P3 | 4132 | 4130 | 41-78 | 0.050 |
| P4 | 4340 | 4344 | 41-80 | 0.090 |

The sequence of Human Albumin precursor was retrieved from the Swiss Prot database (P02768) and exported into the Biolynx software package within MassLynx for examination. The Mature albumin sequence is created by removing the first 18 amino acids as the signal peptide as well as a further 5 amino acids which relate to a pro peptide sequence. The residue numbers indicated refer to the mature protein of 585 amino acids in total. Each observed average Mr value is within 0.1% mass error of the predicted value.

Interestingly, we note that the behaviour of the two 8 kDa species, P1 and P2, is opposite to that observed for the two 4 Kda, P3 and P4. Whilst P1 and P2 are more abundant in control samples, the converse is true for P3 and P4, which are both more abundant in the vCJD group. These observations allow us to develop the hypothesis that secondary fragmentation events, which occur within the Human albumin sequence, might provide an opportunity for a novel class of tractable biomarkers of vCJD and perhaps also other neurological disorders. The hypothesis is outlined in FIG. 4.

Figure 4:
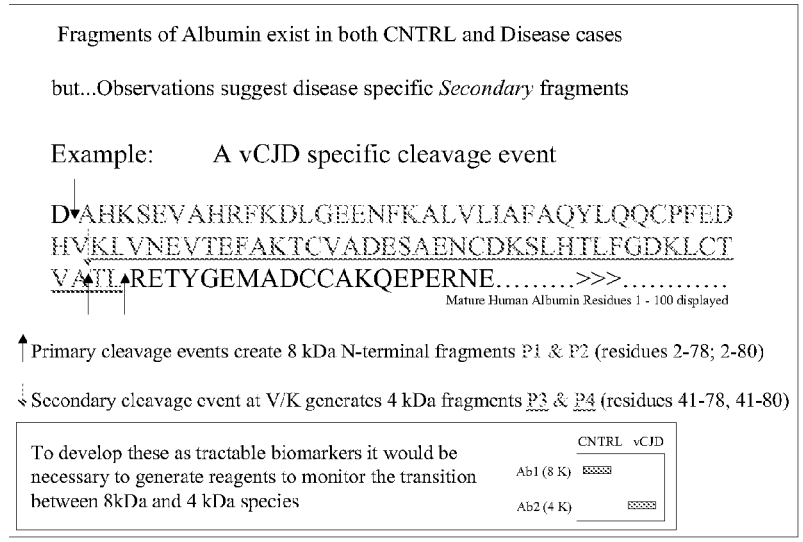
FIG. 4 illustrates fragments of albumin as biomarkers of vCJD.

There are several methods that could be utilised to test the theory described in FIG. 4 and these are outlined below:

Generate antibodies to specific epitopes within the anticipated secondary albumin fragment (SAF-specific monoclonal or polyclonal antibody reagents).

Design multiple reaction monitoring (MRM) transitions to be used during mass spectrometry based validation experiments.

In both instances above, the aim would be to detect and monitor levels of unique biological signatures indicative of disease status.

Example 2

Demonstration of Peptide Cleavage by Normal Human Plasma

Since the observed processing of serum albumin in plasma of vCJD patients was upregulated in disease it follows that there was some minimal processing present in normal control plasma. We have therefore designed an experimental system to measure the production of a lower molecular weight fragment from a model peptide through the proteolytic action of normal human plasma.

1. Introduction

From the initial SELDI data it is thought that cleavage of albumin in human plasma occurs at a -VK- motif within the peptide sequence. Adrenocorticotrophic hormone ACTH (Fragment 18-39; amino acid sequence SEQ ID No. 1: RPVKVYPNGAENESAEFPLEF) is a standard analytical peptide containing the -VK- motif in positions 3 and 4 of its sequence. We therefore developed a mass spectrometry method for the monitoring of ACTH by human plasma.

2. Methods and Materials

To determine the optimal concentration of ACTH for its detection by MALDI-TOF MS and for the detection of its proteolytic product, 20 μL of plasma (~80 μg/μL protein) was added to a range of concentrations of a 0.1 mg/mL solution of ACTH (1 pmol, 750 fmol, 500 fmol, 250 fmol, 100 fmol and 50 fmol) to a total reaction volume of 20.75 μL. Plasma samples were incubated at 37° C. for 60 min. ACTH (750 fmol) provided the optimal concentration for detection and was used to determine the optimal incubation period. Samples were incubated for 30, 40, 50, 60, 90 or 120 min at 37° C. In each case, following incubation the plasma samples were desalted prior to MALDI-TOF MS using the standard protocol.

Two controls were included in the system:
1) 20 μL plasma and equivalent volume of ddH2O to that of ACTH. A spectra was obtained at t=0 min and t=30 min. This was done to ensure that any peak of interest did not arise from plasma.
2) 20 μL ddH2O and 750 fmol ACTH. A spectra was obtained at t=0 min and t=30 min. This was done to ensure that any peak of interest did not arise from ACTH.

The effect of SELDI deactivating buffer on the samples was also analysed, to see if detection of ions of interest was compromised, upon its introduction to the samples. Buffer (20 μL) was added to the reaction mixture after incubation for 60 min at 37° C.

Three different buffers were used:
1.) 6% Sodium Dodecyl Sulphate (SDS)
2.) Lysis Buffer (LB) 9.5 M Urea, 2% CHAPS, 1% Dithiotreithol (DTT)
3.) LB, 9.5 M Urea, 2% CHAPS, 1% DTT plus protease inhibitors (PI).

Peptide mass fingerprints were acquired for all samples in reflectron mode over the m/z range 700-4,000. All spectra were externally calibrated using a lock mass routine based on standard calibrants, to achieve a mass error on ACTH of <100 ppm. Sample solution (0.5 μL) was applied on the target plate with 0.5 μL 2,5-dihydroxybenzoic acid (DHB). A list of monoisotopic peptide masses was obtained for each sample.

3. Results

ACTH at m/z 2465.57 was detected at all concentrations. Cleavage of the peptide at $V_3K_4$ would result in the detection of an ion at m/z 2113.70 (due to the loss of 352 Da i.e. the molecular weight of the three N-terminal amino acids). This ion is visible in all samples containing both plasma and ACTH, with varying degrees of intensity and was not detectable in control samples at t=30 min. This suggests that it has arisen solely from cleavage of ACTH by a species present in the plasma.

Figure 5:
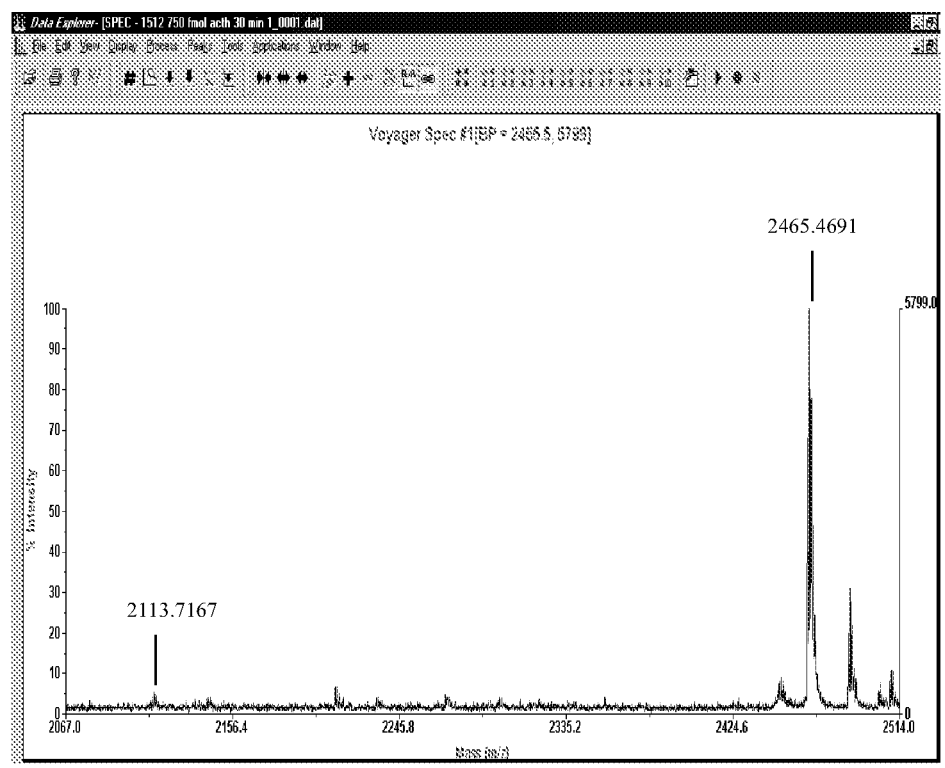
FIG. 5 is a spectrum of ACTH fragments, as described in Example 2.

No ions were visible upon treatment of the samples with 6% SDS. This is due to the negative SDS molecules allowing peptides to bind irreversibly to the C18 stationary phase. Both ACTH m/z 2465.46 and its proteolytic product at m/z 2113.70 were detected in those samples treated with LB and LB+PI. An ACTH concentration of 750 fmol and incubation period of 30 min gave optimal conditions for the detection of ACTH and its proteolytic product. FIG. 5 shows observed spectra for 750 fmol ACTH in 20 μL plasma at t=30 min in reflectron mode. ACTH is detected at m/z 2465.4991 and an ACTH proteolysis product at m/z 2113.7167.

4. Conclusion

Using MALDI-TOF MS and ACTH as a reference peptide we were able to monitor the proteolytic activity in normal plasma by observing a fragment from ACTH (m/z 2113.7167) with the predicted 352 Da loss from the parent peptide mass (m/z 2465.57). This ion represents the loss of the three N-terminal amino acids from the ACTH peptide (m/z 2113.70) supporting the hypothesis that proteolytic activity with specific activity at the -VK- motif is present in plasma.

When we plotted the ratio of the parent mass (m/z 2465.57) to processed mass (m/z 2113.70) we were able to quantitatively assess the kinetics of the cleavage reaction in normal serum. When the same system was used to analyse plasma from vCJD patients this ratio gives a different kinetic allowing for the differentiation between samples derived from patients with vCJD and healthy controls.

Example 3

Design of Improved Peptides for Monitoring of vCJD Associated Proteolytic Activity in Plasma From the studies presented in Example 2 it is apparent that the proteolytic processing of an artificial substrate can be monitored in mass spectrometry. However, the rate of processing and signal intensity would benefit from improvement. To that end we designed further peptides based on the ACTH sequence that would provide for an amplification of the processed peptide signal.

We took the parent ACTH (aa18-38 sequence RPVKVYPNGAENESAEFPLEF (SEQ ID No. 1) and prepared a tetrameric concatamer having the sequence (SEQ ID NO: 2)
KVYPNGAENESAEFPLEFRPVKVYPNGAENESAEFPLEFRPVKVYPNGAE

NESAEFPLEFRPVKVYPNGAENESAEFPLEFRPV which comprises the -VK- motif at residues 21/22, 42/43 & 63/64. This peptide has a mass of 9,860 Da. On cleavage by the plasma protease identified as a marker of vCJD the parent is processed into fragments of 7,395; 4,935; and 2,465 Da. If processing went to completion then the only detectable residue would be at 2,465 Da. Based on this synthetic ACTH derived tetrameric concatemer we were able to determine a differential level of processing between plasma drawn from patients with ACTH compared to normal healthy individuals, with a greater processing of the 9,680 Da parent to the 2,465 Da monomer sequence observed in the vCJD samples.

Such enhanced signal amplification allows for the development of methods based on fluorometric and/or chemiluminescent read outs as described above.

The invention claimed is:

1. A method of diagnosis of variant Creutzfeldt-Jakob disease in a subject, comprising:
   detecting an amount of fragments of a target protein in a diagnostic sample selected from the group consisting of blood, plasma, and serum taken from the subject, the target protein comprising residues 2-78 or 2-80 of serum albumin (Swiss-PROT Accession Number P02768),
   wherein an increase in the amount of fragments of the target protein in the diagnostic sample compared to an amount of fragments of the target protein in a control sample is indicative of variant Creutzfeldt-Jakob disease in the subject.

2. The method according to claim 1, wherein the fragments comprise residues 41-78 or 41-80 of serum albumin.

3. A method of diagnosis of a spongiform encephalopathy selected from Creutzfeldt-Jakob disease (CJD) and variant CJD in a subject, comprising:
   (a) providing a diagnostic sample selected from the group consisting of blood, plasma, and serum taken from a subject and a control sample;
   (b) identifying a protein or fragment thereof that contains a -VK- amino acid pair and is present in the control sample;
   (c) measuring in the control sample and in the diagnostic sample (i) the quantity of fragments of said protein terminating with valine at the C' end; (ii) the quantity of fragments of said protein starting with lysine at the N' end, or (iii) both (i) and (ii); and
   (d) diagnosing the subject as suffering from the spongiform encephalopathy if the quantity of said fragments measured in step (c) is greater in the diagnostic sample than in the control sample.

4. The method according to claim 3, wherein the protein is externally added to the diagnostic sample and the control sample.

5. The method according to claim 4, wherein the protein that is externally added to the diagnostic sample and the control sample is a natural protein.

6. The method according to claim 4, wherein the protein that is externally added to the diagnostic sample and the control sample is a synthetic polypeptide.

7. The method according to claim 3, wherein the protein is naturally present in the control sample.

8. The method according to claim 3, wherein only a single protein containing a -VK- amino acid pair is used in said method of diagnosing spongiform encephalopathy.

9. The method according to claim 3, in which the protein is residues 2-78 or 2-80 of serum albumin (Swiss-PROT Accession Number P02768), and the fragments of the protein are residues 41-78 or 41-80 of the serum albumin.

10. The method according to claim 3, in which the protein is residues 18-38 of ACTH, and the fragment is residues 18-20 of ACTH.

11. The method according to claim 3, in which the protein is SEQ ID NO: 2 and the fragments are residues 1-22, 22-42, 43-63 and 64-84 of SEQ ID NO: 2.

12. The method according to claim 4, wherein the protein that is externally added to the diagnostic sample and the control sample is an immobilized reporter peptide having a detectable label.

13. The method according to claim 12, wherein the step of measuring comprises measuring in the control sample and in the diagnostic sample (i) the quantity of immobilized reporter peptide fragments, (ii) the quantity of liberated reporter peptide fragments, or (iii) both (i) and (ii).

14. The method according to claim 13, in which the liberated reporter peptide fragment comprise the detectable label.

15. The method according to claim 12, wherein the detectable label straddles a cleavage point in the immobilized reporter peptide, and wherein the detectable label comprises a cooperating pair of reporter groups that are separated upon cleavage of the immobilized reporter peptide such that the immobilized and liberated fragments of the immobilized reporter peptide comprise a reporter group each.

16. The method according to claim 15, wherein the step of measuring comprises measuring the quantity of signal generated when the cooperating pair is separated upon cleavage of the immobilized reporter peptide.

17. The method according to claim 15, wherein the step of measuring comprises measuring the quantity of signal generated when the cooperating pair of reporter groups is together in the immobilized reporter peptide, and measuring the loss of signal when the cooperating pair is separated upon cleavage of the immobilized reporter peptide.

18. A method of diagnosis of variant Creutzfeldt-Jakob disease in a subject, comprising:
   a) obtaining a diagnostic sample selected from the group consisting of blood, serum and plasma taken from a subject and a control sample;
   b) admixing a protein containing a -VK- amino acid pair with the diagnostic sample and the control sample;
   c) measuring in the control sample and in the diagnostic sample (i) the quantity of fragments of said protein terminating with valine at the C' end, (ii) the quantity of fragments of said protein starting with lysine at the N' end, or (iii) both (i) and (ii); and
   d) diagnosing the subject as suffering from the variant Creutzfeldt-Jakob disease if the quantity of said fragments measured in step (c) is greater in the diagnostic sample than in the control sample.

* * * * *

SEQUENCE LISTING

```
<160> NUMBER OF SEQ ID NOS: 3

<210> SEQ ID NO 1
<211> LENGTH: 21
<212> TYPE: PRT
<213> ORGANISM: Unknown
<220> FEATURE:
<223> OTHER INFORMATION: Description of Unknown: Adrenocorticotrophic
      hormone peptide

<400> SEQUENCE: 1

Arg Pro Val Lys Val Tyr Pro Asn Gly Ala Glu Asn Glu Ser Ala Glu
1               5                   10                  15

Phe Pro Leu Glu Phe
            20

<210> SEQ ID NO 2
<211> LENGTH: 84
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Lys Val Tyr Pro Asn Gly Ala Glu Asn Glu Ser Ala Glu Phe Pro Leu
1               5                   10                  15

Glu Phe Arg Pro Val Lys Val Tyr Pro Asn Gly Ala Glu Asn Glu Ser
            20                  25                  30

Ala Glu Phe Pro Leu Glu Phe Arg Pro Val Lys Val Tyr Pro Asn Gly
        35                  40                  45

Ala Glu Asn Glu Ser Ala Glu Phe Pro Leu Glu Phe Arg Pro Val Lys
    50                  55                  60

Val Tyr Pro Asn Gly Ala Glu Asn Glu Ser Ala Glu Phe Pro Leu Glu
65                  70                  75                  80

Phe Arg Pro Val

<210> SEQ ID NO 3
<211> LENGTH: 100
<212> TYPE: PRT
<213> ORGANISM: Homo sapiens

<400> SEQUENCE: 3

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
```

-continued

```
                85                  90                  95
Glu Arg Asn Glu
            100
```